(12) United States Patent
Lischinsky et al.

(10) Patent No.: US 9,844,682 B2
(45) Date of Patent: Dec. 19, 2017

(54) SKIN TREATMENT DEVICES AND METHODS

(71) Applicant: EndyMed Medical Ltd., Caesarea (IL)

(72) Inventors: Daniel Lischinsky, Ramat Ishay (IL); Yoram Harth, Herzlya (IL)

(73) Assignee: ENDYMED MEDICAL LTD., Caesarea (IL)

( * ) Notice: Subject to any disclaimer, the term of this patent is extended or adjusted under 35 U.S.C. 154(b) by 320 days.

(21) Appl. No.: 13/922,254

(22) Filed: Jun. 20, 2013

(65) Prior Publication Data
US 2013/0282085 A1    Oct. 24, 2013

Related U.S. Application Data

(63) Continuation-in-part of application No. 13/865,658, filed on Apr. 18, 2013, now abandoned, which is a
(Continued)

(51) Int. Cl.
*A61B 18/12* (2006.01)
*A61N 5/00* (2006.01)
(Continued)

(52) U.S. Cl.
CPC ............ *A61N 5/00* (2013.01); *A61B 18/1206* (2013.01); *A61B 18/14* (2013.01); *A61N 1/28* (2013.01);
(Continued)

(58) Field of Classification Search
CPC ............ A61B 18/1206; A61B 18/1233; A61B 18/1477; A61B 2018/00577;
(Continued)

(56) References Cited

U.S. PATENT DOCUMENTS 5,334,193 A    8/1994 Nardella
5,383,917 A    1/1995 Desai et al.
(Continued)

FOREIGN PATENT DOCUMENTS

CN    202207398    5/2012
EP    2291223    3/2011
(Continued)

OTHER PUBLICATIONS

PCT Search Report dated Jul. 20, 2015 for PCT application PCT/IL2015/050289.
(Continued)

*Primary Examiner* — Michael Peffley
(74) *Attorney, Agent, or Firm* — Pearl Cohen Zedek Latzer Baratz LLP

(57) ABSTRACT

A skin treatment device for home use is provided herein. The device has enhanced safety features and improved operation efficiency. RF energy is delivered under strict control to a relatively small and well localized volume of the skin, avoiding excessive heating of the skin surface. Surface heating is monitored both by direct temperature measurement and by movement monitoring of the device to ensure proper use and prevent skin overheating and the pain associated therewith.

16 Claims, 9 Drawing Sheets

Related U.S. Application Data continuation of application No. 12/802,518, filed on Jun. 7, 2010, now abandoned, which is a continuation-in-part of application No. 11/654,914, filed on Jan. 17, 2007, now Pat. No. 8,206,381.

(60) Provisional application No. 61/665,552, filed on Jun. 28, 2012, provisional application No. 61/213,409, filed on Jun. 5, 2009, provisional application No. 61/213,410, filed on Jun. 5, 2009, provisional application No. 60/759,289, filed on Jan. 17, 2006, provisional application No. 60/774,167, filed on Feb. 17, 2006.

(51) Int. Cl.
*A61B 18/14* (2006.01)
*A61N 1/32* (2006.01)
*A61N 1/28* (2006.01)
*A61N 7/00* (2006.01)
*A61B 18/00* (2006.01)
*A61N 1/04* (2006.01)

(52) U.S. Cl.
CPC ...... *A61N 1/328* (2013.01); *A61B 2018/0075* (2013.01); *A61B 2018/00452* (2013.01); *A61B 2018/00476* (2013.01); *A61B 2018/00678* (2013.01); *A61B 2018/00702* (2013.01); *A61B 2018/00791* (2013.01); *A61B 2018/00869* (2013.01); *A61B 2018/00875* (2013.01); *A61B 2018/1273* (2013.01); *A61B 2018/1467* (2013.01); *A61N 1/0408* (2013.01); *A61N 7/00* (2013.01); *A61N 2007/0008* (2013.01)

(58) Field of Classification Search
CPC  A61B 2018/00767; A61B 2018/00779; A61B 2018/00827; A61B 2018/124; A61B 2018/143; A61B 2018/00589; A61B 2018/00476; A61B 2018/00708
See application file for complete search history.

(56) References Cited

U.S. PATENT DOCUMENTS

| | | | |
|---|---|---|---|
| 5,462,545 A | | 10/1995 | Wang et al. |
| 5,620,481 A | * | 4/1997 | Desai ............... A61B 18/1492 606/31 |
| 5,630,426 A | | 5/1997 | Eggers |
| 5,755,753 A | | 5/1998 | Knowlton |
| 6,042,580 A | | 3/2000 | Simpson |
| 6,059,778 A | * | 5/2000 | Sherman ............ A61B 18/1206 606/34 |
| 6,106,524 A | | 8/2000 | Eggers |
| 6,139,569 A | * | 10/2000 | Ingle .................. A61B 18/14 607/104 |
| 6,210,406 B1 | | 4/2001 | Webster |
| 6,228,078 B1 | | 5/2001 | Eggers et al. |
| 6,387,380 B1 | * | 5/2002 | Knowlton ............ A61B 18/12 128/898 |
| 6,413,255 B1 | * | 7/2002 | Stern ................. A61B 18/14 606/41 |
| 6,786,906 B1 | | 9/2004 | Cobb |
| 8,206,381 B2 | | 6/2012 | Lischinsky et al. |
| 2001/0008967 A1 | | 7/2001 | Sherman |
| 2002/0120261 A1 | * | 8/2002 | Morris ............... A61B 18/1477 606/41 |
| 2005/0222565 A1 | * | 10/2005 | Manstein ........... A61B 18/1477 606/41 |
| 2007/0088413 A1 | | 4/2007 | Weber et al. |
| 2007/0293918 A1 | | 12/2007 | Abbott et al. |
| 2008/0183251 A1 | | 7/2008 | Azar et al. |
| 2008/0312651 A1 | | 12/2008 | Pope et al. |
| 2011/0015625 A1 | | 1/2011 | Adanny et al. |
| 2011/0245735 A1 | | 10/2011 | Eckhouse et al. |
| 2013/0282085 A1 | | 10/2013 | Lischinsky et al. |
| 2013/0289679 A1 | | 10/2013 | Eckhouse et al. |

FOREIGN PATENT DOCUMENTS

| | | |
|---|---|---|
| JP | 2011-004882 | 1/2011 |
| KR | 101065611 | 9/2011 |
| WO | WO 2007/046886 | 4/2007 |
| WO | WO 2009/126117 | 10/2009 |
| WO | WO 2012/052986 | 4/2012 |

OTHER PUBLICATIONS

GB Search Report dated Jan. 19, 2015 for GB application 1410954.0.
Office Action dated Apr. 6, 2016 for U.S. Appl. No. 14/220,315.
Office Action dated Nov. 23, 2016 for U.S. Appl. No. 14/220,315.
Office Action dated Feb. 2, 2012 for U.S. Appl. No. 12/802,518.
Office Action dated Oct. 18, 2012 for U.S. Appl. No. 12/802,518.
Office Action dated Nov. 2, 2015 for U.S. Appl. No. 13/865,658.
European Search Report dated Oct. 9, 2017 for corresponding European Application 15764373.5 filed Mar. 19, 2015.

* cited by examiner

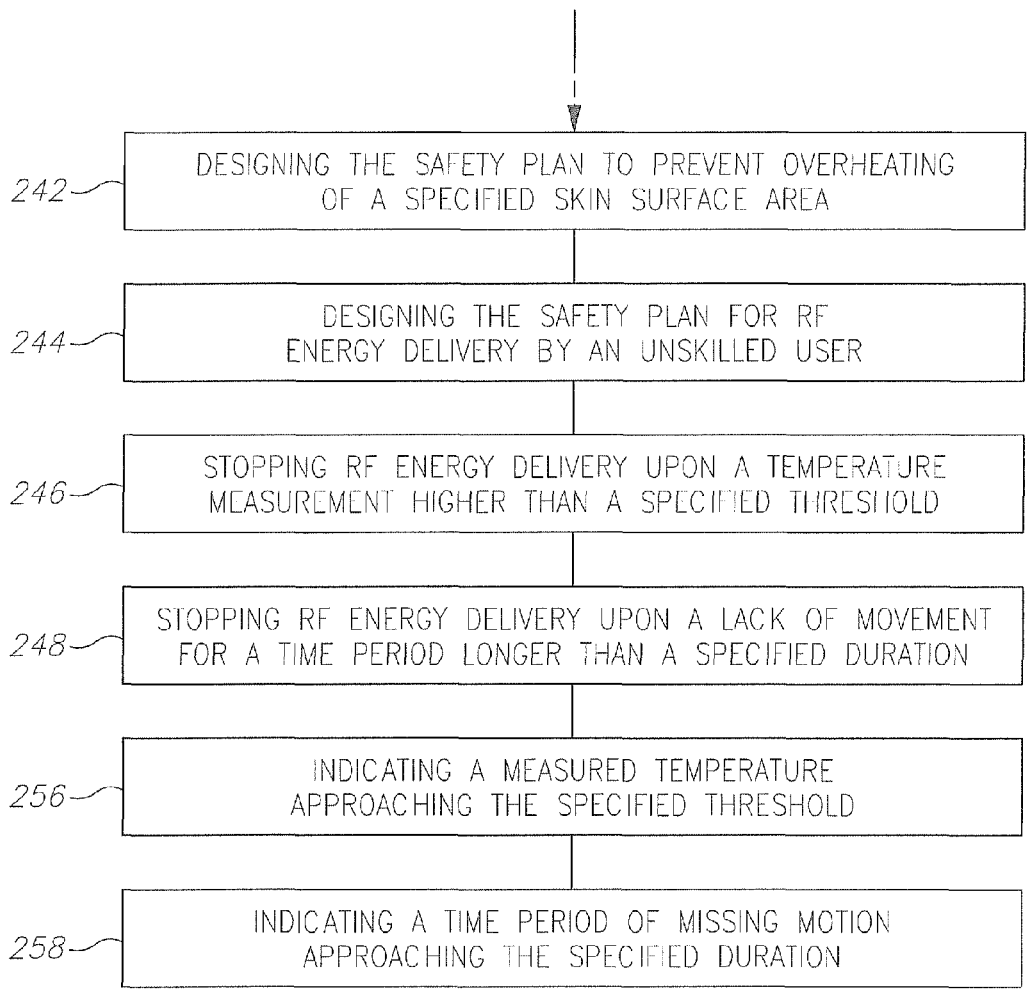
Figure 6 (cont. 1)

SKIN TREATMENT DEVICES AND METHODS

CROSS REFERENCE TO RELATED APPLICATIONS

This application claims the benefit of U.S. Provisional Patent Application No. 61/665,552, filed Jun. 28, 2012, which is incorporated herein by reference in its entirety. This application is also a continuation in part of U.S. patent application Ser. No. 13/865,658, filed on Apr. 18, 2013, which is a continuation of U.S. patent application Ser. No. 12/802,518, filed on Jun. 7, 2010, which claims priority under 35 U.S.C. §119 to U.S. Provisional Patent Application No. 61/213,409, filed Jun. 5, 2009, and to U.S. Provisional Patent Application No. 61/213,410, filed Jun. 5, 2009. U.S. patent application Ser. No. 12/802,518, now abandoned, is also a continuation-in-part application of U.S. patent application Ser. No. 11/654,914, filed Jan. 17, 2007, now U.S. Pat. No. 8,206,381, which claims priority under 35 U.S.C. §119 to U.S. Provisional Patent Application No. 60/759,289, filed Jan. 17, 2006, and to U.S. Provisional Patent Application No. 60/774,167, filed Feb. 17, 2006. Each noted application is herein incorporated by reference in its entirety.

BACKGROUND

1. Technical Field

The present invention relates to the field of skin treatment, and more particularly, to radiofrequency (RF) skin treatment.

2. Discussion of Related Art

Energy emitting devices are typically used to heat cutaneous or subcutaneous tissues or to trigger a non-thermal chemical or photochemical reaction. In many cases, heating of the epidermis should be limited to prevent skin burns. This, in turn, limits the amount of energy that is delivered to deeper tissues. In a professional clinic setting, energy emitting skin treatment devices use skin cooling to prevent over heating of the epidermis. Due to the high cost and the size of a device which incorporates such functionality, active cooling is not practical in consumer, home-use devices.

U.S. Pat. No. 8,206,381, which is incorporated herein by reference in its entirety, discloses an electrosurgical device for applying phase controlled RF energy to a treatment site.

BRIEF SUMMARY OF THE INVENTION

One aspect of the present invention provides a skin treatment device comprising a plurality of linearly arranged electrodes applicable to a user's skin; a radio frequency (RF) generator, arranged to deliver RF energy to the skin via the electrodes; and a control unit arranged to control RF energy delivery by the RF generator to the skin according to a specified transmission plan and/or a specified safety plan.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1:
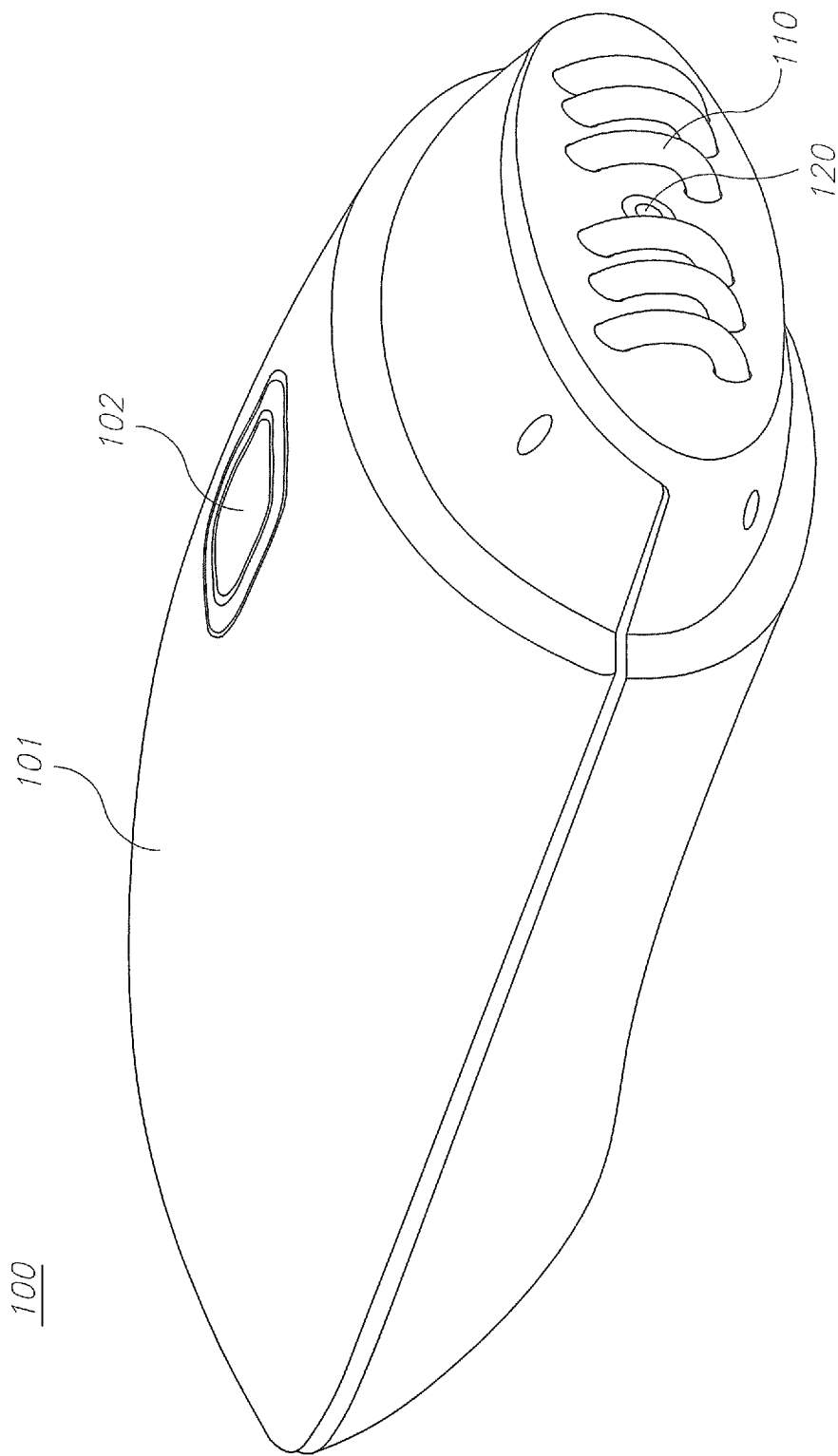
FIGS. 1 and 3 are high level schematic perspective illustrations of skin treatment devices according to some embodiments of the invention.

Prior to setting forth the detailed description, it may be helpful to set forth definitions of certain terms that will be used hereinafter.

The term "skin treatment" as used in this application refers to any type of skin treatment such as skin heating, treating wrinkles or rhytides, treating skin aging by collagen remodeling, treating diseases of the skin such as acne and psoriasis, treating skin roughness, treating skin pigmentation, skin peeling, epidermal skin rejuvenation or providing any other therapeutic effect.

The term "phase" as used in this application refers to any value of the relative angle of a fluctuating current or voltage. The terms "phase control" or "controlling the phase" of the delivered current or voltage, as used herein in this application, refer to setting a specific phase value to delivered current or voltage. The specific phase value may be any value from 0° to 360° (0 to $2\pi$ radians). The term "relative phase" between electrodes, as used herein in this application, refers to any phase difference between electrodes, including a zero phase difference.

The term "polarity" as used in this application in relation to electrodes refers to the electrode being a positive pole or a negative pole with respect to current delivery. The term "same polarity" as used in this application with reference to two electrodes refers to the two electrodes having the same polarity during most of the time, i.e., the two electrodes being in the same polarity longer than they are in opposite polarities, or, using phase terms, have a phase difference between +90° and −90° (−$\pi$/2 to +$\pi$/2 radians). The signs + and − as used in this application to refer to electrode polarities schematically designate which electrodes have the same polarity, in the sense explained above. The phase between electrodes having the same sign may be zero but may also have any value between +90° and −90° (−$\pi$/2 to +$\pi$2 radians). Different electrodes in the + or − groups may have different phase difference values between them. Some or all of the electrodes in each of the + or − groups may have a zero phase difference between them.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Embodiments of the invention provide a skin treatment device for home use having enhanced safety features and improved operation efficiency. RF (radiofrequency) energy is delivered under strict control to a relatively small and well localized volume of the skin, avoiding excessive heating of the skin surface. Surface heating is monitored both by direct temperature measurement and by movement monitoring of the device to ensure proper use and prevent skin overheating and the pain associated therewith. Presented devices and methods allow safer and more effective implementation of energy delivery to the skin in a consumer, home setting.

Figure 2A:
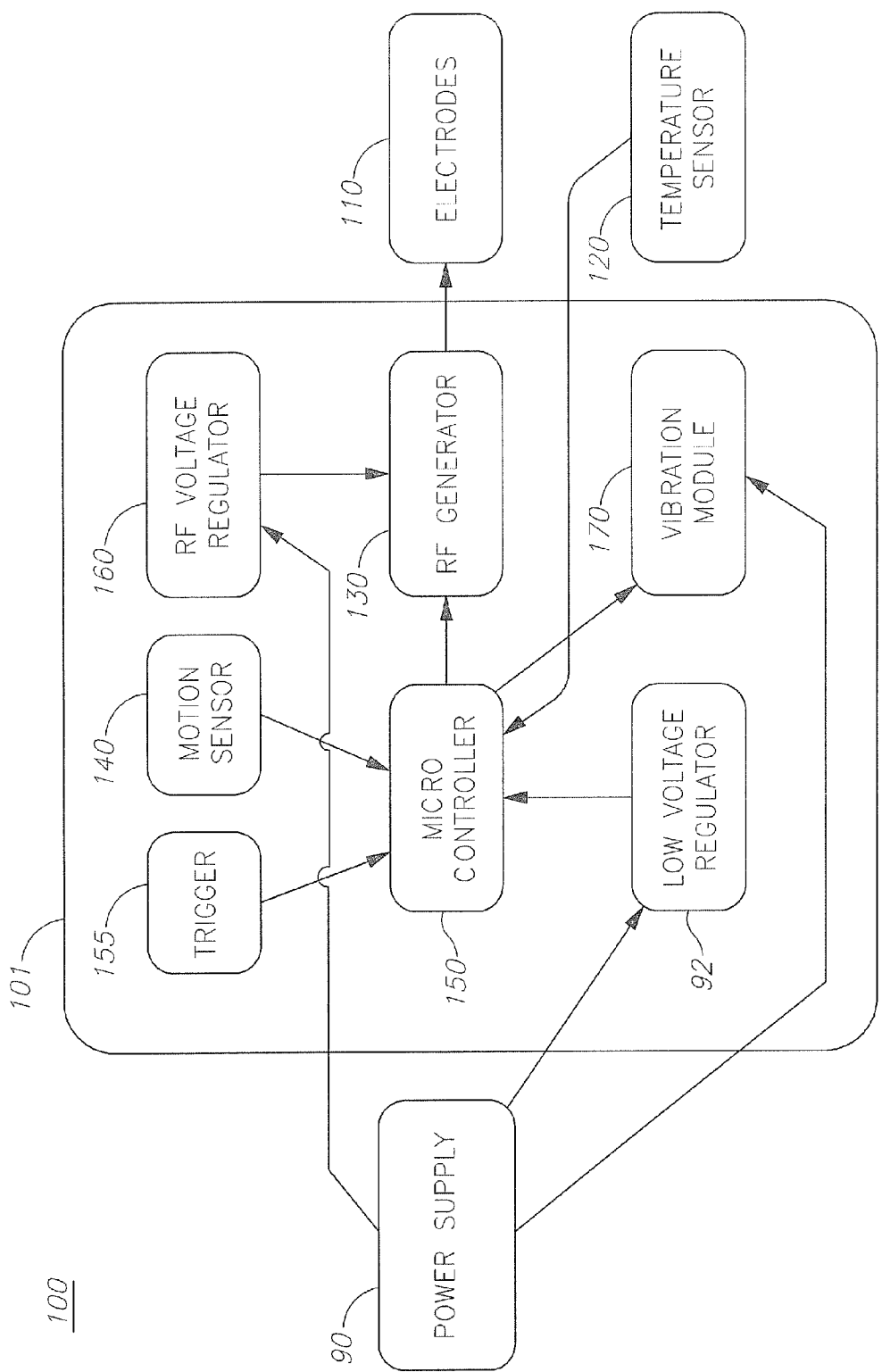
FIG. 2A is a high level schematic block diagram of a skin treatment device according to some embodiments of the invention.
Figure 2B:
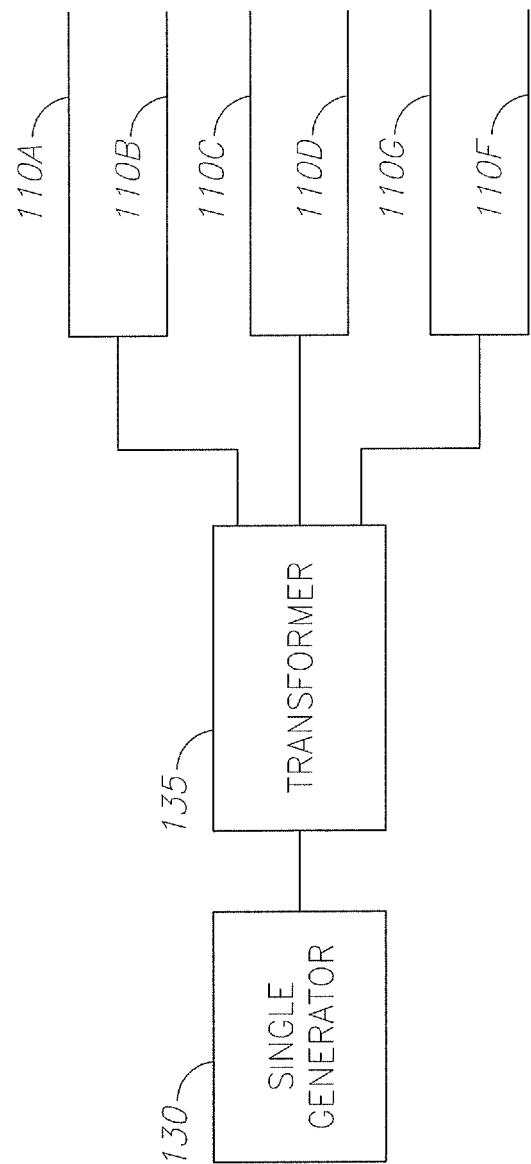
FIG. 2B is a high level schematic illustration of an electrode arrangement in a skin treatment device according to some embodiments of the invention.
Figure 3:
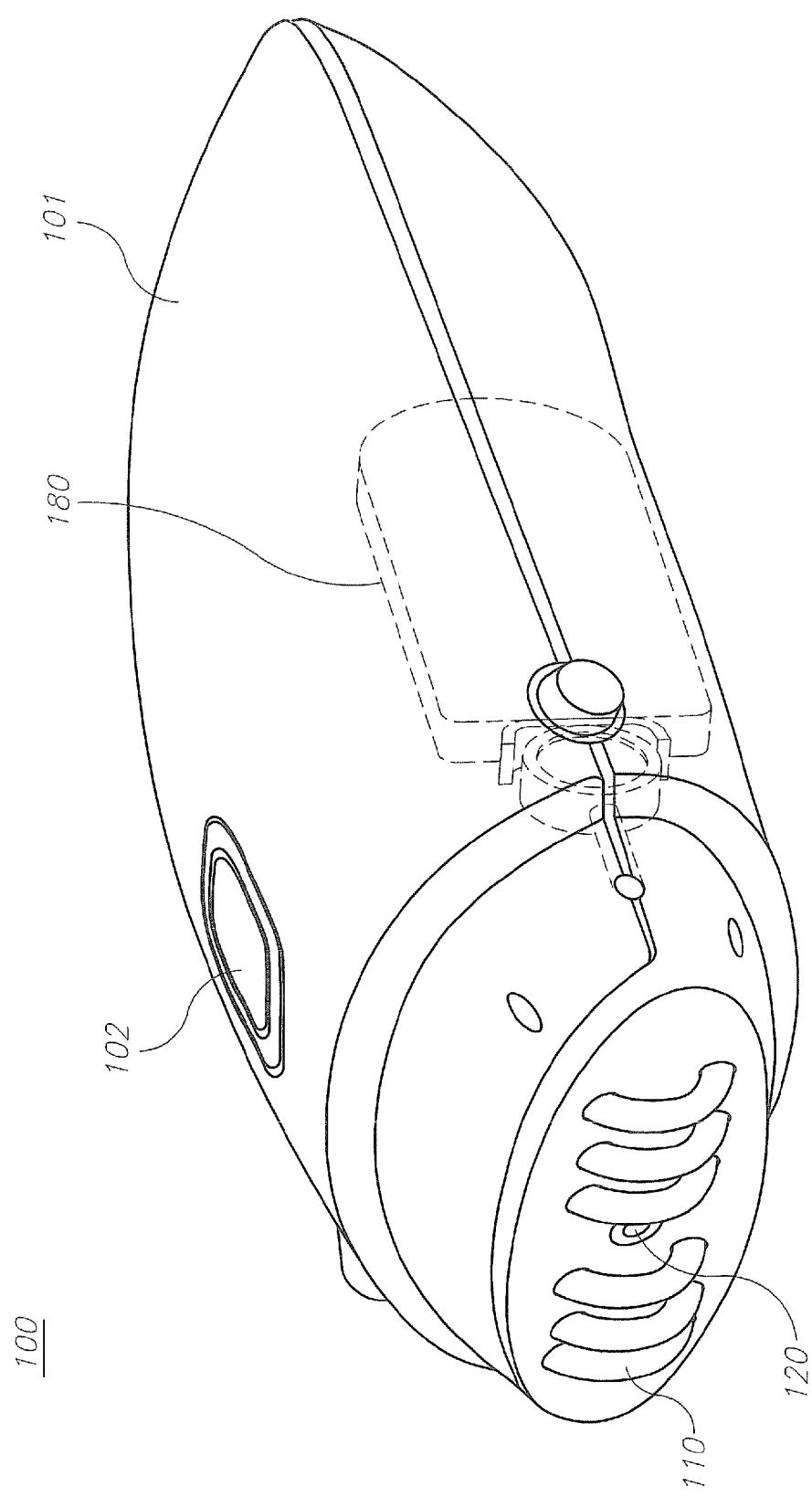

FIGS. 1 and 3 are high level schematic perspective illustrations of skin treatment devices 100 according to some embodiments of the invention, FIG. 2A is a high level schematic block diagram of skin treatment device 100 according to some embodiments of the invention, and FIG. 2B is a high level schematic illustration of an electrode arrangement in a skin treatment device according to some embodiments of the invention. Devices 100 may be designed to controllably heat a specific skin volume while keeping the surface of the skin below a specified temperature threshold.

Skin treatment device 100 comprises a plurality of electrodes 110 applicable to a user's skin. Electrodes 110 may be linearly arranged. A housing 101 of device 100 may be arranged to hold electrodes 110 and electronic circuitry as described below. Housing 101 may be ergonomically designed, for example to apply the treatment in a paintbrush-like continuous manner. Housing 101 may comprise a mechanism that assures contact of electrodes 110 with the skin. Device 100 may be operated by pressing button 102. Device 100 may be arranged to operate at different intensities by pressing button 102 at different patterns (repeatedly, continuously etc.).

Skin treatment device 100 further comprises a radio frequency (RF) generator 130, arranged to deliver RF energy to the skin via electrodes 110. RF generator 130 may be supplied by an external power supply 90, by an internal power supply, by inductive power supply, etc. RF generator 130 may be regulated by RF voltage regulator 160 and controlled by a control unit 150 such as a micro controller. Control unit 150 may be associated with a trigger 155 and a low voltage regulator 92.

Skin treatment device 100 further comprises control unit 150 arranged to control RF energy delivery by RF generator 130 to the skin according to a specified transmission plan. Control unit 150 may be further arranged to control the phase of each electrode and to coordinate the polarities of the electrodes. Hence, control unit 150 may be arranged to set any specified phase between any two electrodes to exactly control energy delivery to the skin. In particular, control unit 150 may designate reversed polarities to subgroups of the electrodes, as denoted in the following by the signs + and −. The reversed polarities may be approximate (i.e., not necessarily 180° but also, e.g., 120° or 160° etc.) as explained above. The phase differences between the electrodes may be pre-determined and controlled during operation. The transmission plan may comprise controlling relative electrode polarities to concentrate the delivered RF energy to a specified skin volume. For example, the relative electrode polarities may be controlled to yield one or two pairs of adjacent electrodes 110 with substantially the same polarity (see examples below).

In certain embodiments, electrodes 110A-110F are all connected via a transformer 135 or single generator 130. Such configurations may be practical in home use devices because they require only a single generator and make use of both electrodes of each pair (commercial devices for use in professional clinic settings usually have multiple generators and are commonly grounded such that only one of the electrodes of each pair contacts the skin). In certain embodiments, some of electrodes 110A-110F may be connected together to improve current delivery and heating according to the principles explained below. Thus, devices 100 having a specified number electrodes may be used to deliver RF energy via a smaller number of electrodes by interconnecting some of the electrodes. The examples below, relating to configurations of four and of six electrodes, should be interpreted in a non-limiting manner as relating to any number of electrodes.

Figure 4:
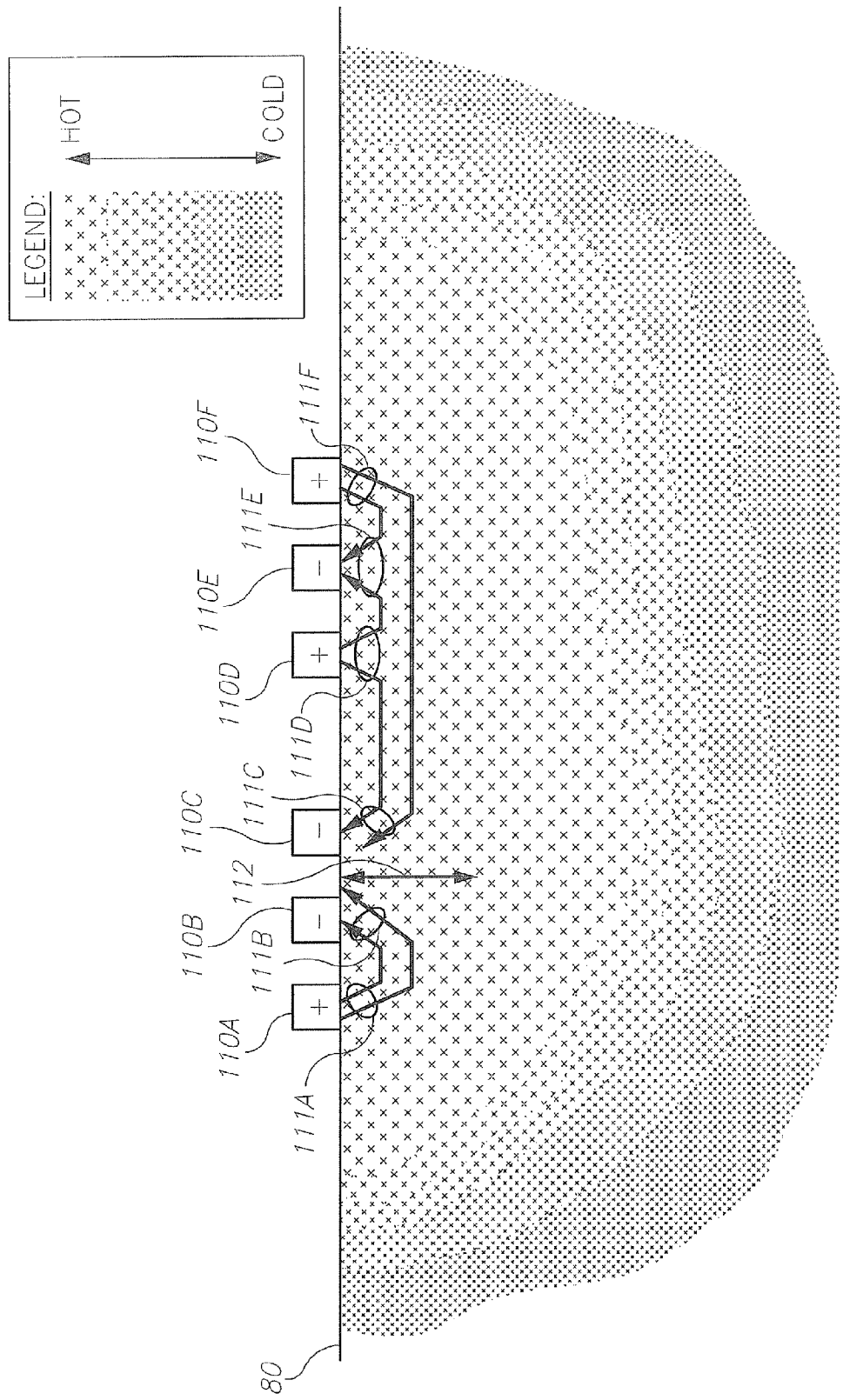
FIG. 4 is a high level schematic illustration of an operating principle of a skin treatment device according to some embodiments of the invention.

FIG. 4 is a high level schematic illustration of an operating principle of skin treatment device 100 according to some embodiments of the invention. Linearly arranged electrodes 110 are denoted 110A-110F in their arrangement order on skin 80. Electrode polarity is designated +−−+−+ which is the only configuration (from possible configurations being: +−+−+−; +−−+−+; +−−++−, +−++−−++−+−−+++−−− under application of left to right and + to − symmetries) which exhibits alternating polarities to all but one adjacent pairs of electrodes 110. The one adjacent pair of electrodes having the same polarity in the illustrated case are electrodes 110I, 110C. In certain embodiments, device 100 may comprise 2, 3, 4 or more pairs of electrodes 110.

FIGS. 5A-5G are high level illustrations of electrode configurations and estimated resulting current distributions, based on simulations and presented qualitatively.

FIG. 4 schematically illustrates RF energy delivered to the skin in form of schematic current designations 111A-111F relating to electrodes 110A-110F respectively. Schematically, positive electrodes 110A, 110D, 110F emanate currents and negative electrodes 110B, 110C, 110E receive currents. Clearly electrode polarities continuously fluctuate so that current 111 continuously change direction and magnitude, and FIG. 4 should be taken as a non-limiting illustrative explanation. Each electrode current is symbolized by two currents to schematically illustrate the relations among the electrodes. The inventors have invested significant amount of research to study the possible electrode configurations and to show that the presented configuration results in RF energy delivered principally to a relatively small skin volume below the pair of electrodes 110B, 110C having the same polarity. The effective energy that heats the skin volume is illustrated by arrow 112. The delivered heat is schematically illustrated by a variable raster density (based on three dimensional Maxwell simulations), which shows a clear concentration of energy below electrodes 110, 110C. FIG. 4 is a schematic representation of experimental data derived for the presented electrode configuration.

Without wishing to be bound by theory, the inventors point out that the spatial configuration and the phase configuration of electrodes 110 are understood to determine the heating pattern of the treated skin for given skin characteristics. In particular, as larger electric currents tend to flow through regions of lower impedance, controlling the phase and the polarity of electrodes 110 allows controlling the extent of tissue heating. For example, each of two adjacent electrodes having the same polarity (i.e., electrodes that are substantially in phase with each other) increases the impedance the other electrode experiences at the tissue region between the electrodes. Hence, pairs of electrodes with the same polarity create electrical potential barriers 113 with increased impedance between the electrodes. Barriers 113 tend to drive the electric currents associated with the pair of electrodes deeper into the skin tissue (e.g., at an angle to the skin surface), as the increased impedance is experienced closer to the electrodes and hence closer to the surface.

Figure 5A:
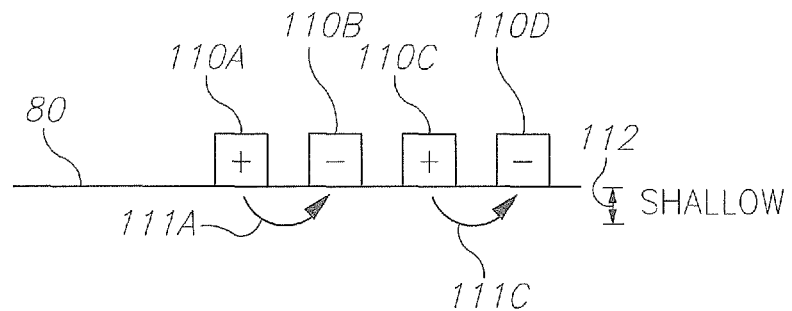
FIGS. 5A-5G are high level illustrations of electrode configurations and estimated resulting current distributions, based on simulations and presented qualitatively.
Figure 5B:
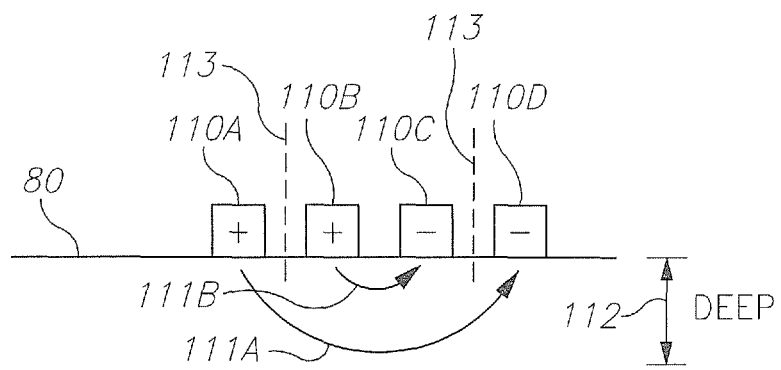

FIGS. 5A and 5B illustrate two configurations with four electrodes. In each configuration, two pairs of the electrodes have the same polarity. As illustrated in FIG. 5A, when the polarity alternates between the electrodes the created currents and generated heating are relatively shallow in the skin, as each electrode has an adjacent electrode with reversed polarity. On the other hand, as illustrated in FIG. 5B, when the electrodes are arranged in two pairs of the same polarity, impedance barriers 113 are formed between the electrodes of each such pair, and the currents penetrate deeper into the skin.

FIGS. 5C-5G illustrate possible configurations for six electrodes, denoted schematically as +-+-+-, +---+-+, +-++--, +++--- and ++-+-- respectively. It is noted that for symmetry reasons, reversing all polarities in a configuration yields an equivalent configuration (as RF current fluctuates) and reversing the sequence of the electrodes also yields an equivalent configuration (as the device may be used in either direction).

Figure 5C:
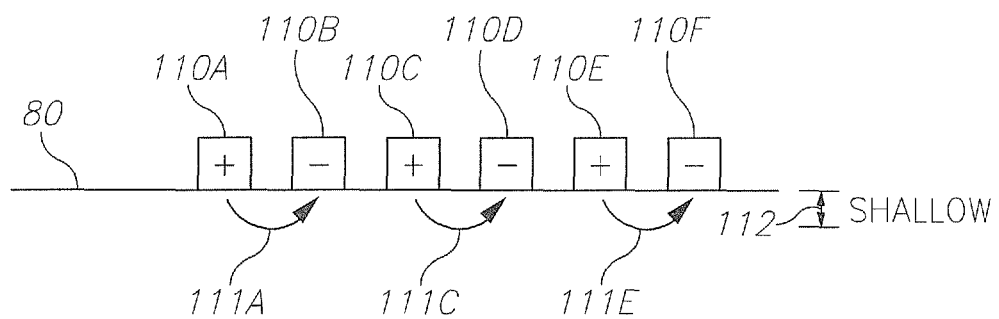
Figure 5D:
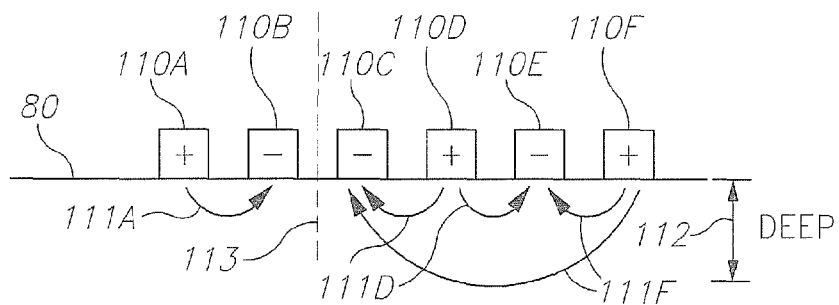
Figure 5E:
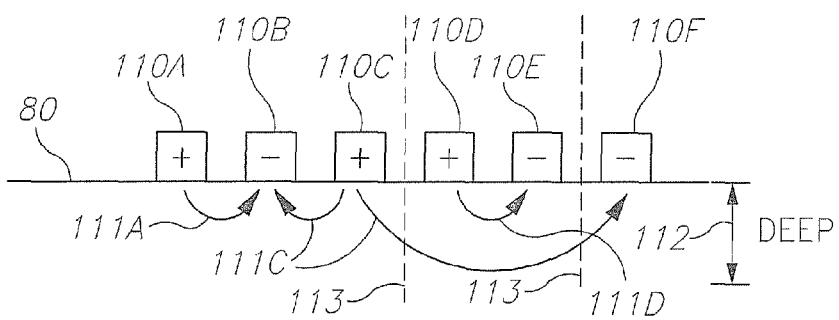
Figure 5F:
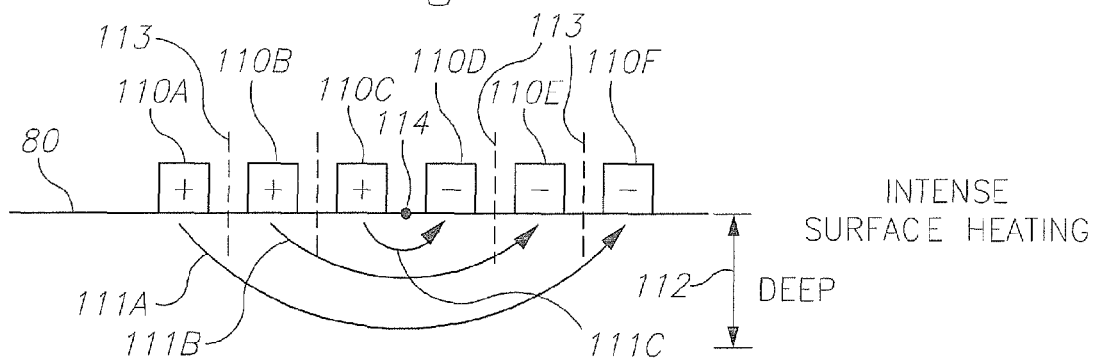
Figure 5G:
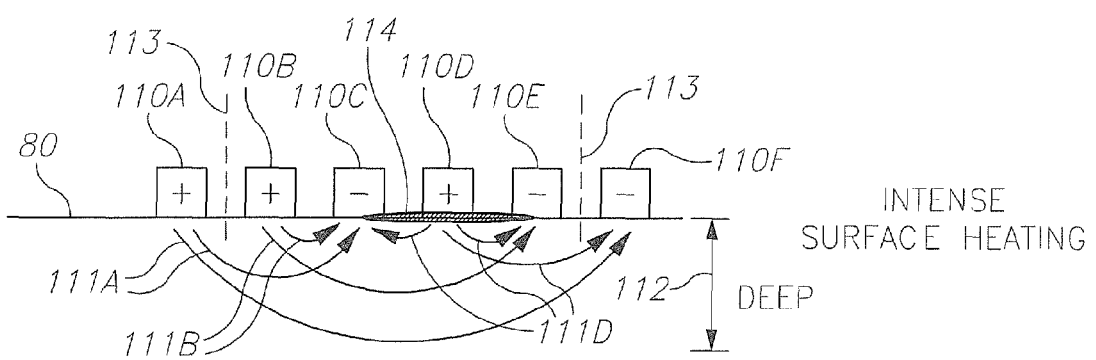

The configurations of FIGS. 5C and 5F enhance the effects discussed above for the four electrodes configurations illustrated in FIGS. 5A and 5B respectively. The configuration illustrated in FIG. 5C generates shallow currents and shallow heating, while the configuration illustrated in FIG. 5F generates deep currents due to the multiple increased-impedance barriers 113 but also intense surface heating at region 114 due to the convergence of currents from all pairs of electrodes. FIGS. 5E and 5G illustrate two configurations with two impedance barriers, both of which yield deep currents causing deep heating of the skin tissue. The configuration illustrated in FIG. 5G creates however intense surface heating as increased-impedance barriers 113 are lateral and currents are concentrated towards the center of the configuration. Finally, FIG. 5D illustrates a configuration with a single increased-impedance barrier 113 that suffices to yield deep currents and heating but avoids intensive surface heating. Simulation results of this configuration were presented in detail in FIG. 4 and clearly illustrate the efficiency of such a configuration.

The configurations presented above are non-limiting examples for configurations with four and six electrodes. They are not to be taken as limiting the number of electrodes but as indicating plausible configurations of larger numbers of electrodes.

In embodiments, control unit 150 may be further arranged to derive a realtime estimation of skin impedance and adjust the delivered energy according to the estimated skin impedance, resulting in more predictable results. The skin impedance estimation may be derived from measuring energy delivery with respect to applied voltage (skin impedance increases with the treated skin volume). Different energy delivery parameters may be applied to treating different skin region (e.g., in the face, the eye region is characterized by thin skin in the range of 1 mm, while the cheek region is characterized by thin skin in the range of 3-4 mm).

In certain embodiments, skin treatment device 100 may further comprise a temperature sensor 120 positioned in a vicinity of electrodes 110 and a motion sensor 140 arranged to measure movements of electrodes 110 with respect to the skin. Motion sensor 140 may be arranged to measure electrode movements by measuring the movements of whole device 100. For example, motion sensor 140 may be an accelerometer. In certain embodiments, control unit 150 may further control RF energy delivery with respect to measurements obtained from the temperature and motion sensors according to a specified safety plan designed to prevent overheating of a specified skin surface area upon operation of device 100 by an unskilled user. For example, control unit 150 may be arranged to stop energy delivery upon detection of a non-changing measurement from at least one of temperature sensor 120 and motion sensor 140. Such may indicate either malfunctioning of one of sensors 121, 140 or inappropriate usage of device 100, e.g., due to lack of skill. As either of these situations may harm the user, energy delivery is stopped.

Alternatively or additionally, an indicator (not shown) may be arranged to indicate non-changing measurements and indicate possible user actions to solve such problems. In certain embodiments, the safety plan may be devised to create enough thermal effect to induce collagen remodeling while avoiding any ablative thermal damage in the epidermis, dermis or hypodermis. In certain embodiments, the indicator may be part of a user interface (not shown) including, for example, an LED indicator which lets the user know that device 100 is ready for use, a blinking LED indicates active RF emission, a timer which stops RF emission after a predetermined period of time (e.g., between about 1-10 minutes, between 1 and 4 minutes, and about 4 minutes, and similar time periods) and an auditory and/or vibratory signal means (e.g., mobile phone vibration mechanism, speaker, and the like), which signals, for example, to the user that the treatment time per area is over (e.g., 4 minutes).

In certain embodiments, temperature sensor 120 may separate electrodes 110 into two groups, one of which comprising the one adjacent pair of electrodes with the same polarity (e.g. 110B, 110C). Electrodes 110 and temperature sensor 120 may be arranged in a line with a central temperature sensor. The specified transmission plan may be designed to maximize the RF energy delivery to a specified skin volume below one of the two electrode groups. In certain embodiments, device 100 may comprise additional temperature sensors.

The combination of motion sensor 140 and temperature sensor 120 overcomes several problems associated with using only a temperature sensor. Such problems include a relatively long reaction time of the temperature sensor (damage may occur within the reaction time) and measurement at locations which do not experience the highest temperature during treatment (due to sensor position apart of the electrodes and device movements). Monitoring device motion by motion sensor 140 compensates for such problems by ensuring an averaging both of actual heating (by moving electrodes 110) and of temperature measurements (by measuring all over the heated region). Using temperature sensor 120 in addition to motion sensor 140 overcomes several problems associated with using only a motion sensor, in particular the lack of temperature monitoring. Moreover, measuring to independent parameters is more robust to the effects variability in skin characteristics (e.g., skin thickness and impedance) and energy delivery parameters. Such robustness is particularly of importance in home usage.

In certain embodiments, the specified safety plan may be configured to keep a surface of the skin below a specified temperature threshold, for example the specified safety plan may comprise stopping RF energy delivery upon detection of a temperature measurement higher than a specified threshold (e.g., 42.5° C. or 43° C.) or a lack of movement for a time period longer than a specified duration. Skin treatment device 100 may further comprise an indicator (not shown) arranged to indicate the detection of such measurements.

In certain embodiments, a fluid or a gel may be used during skin treatment with device 100 to facilitate any of: better skin treatment, better heat dispersion, better electric contact to the electrodes, skin cooling, etc. In certain embodiments, device 100 may further comprise a fluid dispenser 180 arranged to dispense, upon actuation, a fluid, a gel or a cream on the skin. In certain embodiments, temperature measurement may be carried out by a temperature sensitive fluid applied on the skin in addition or to temperature sensor 120. In certain embodiments, temperature sensor may be implemented as a temperature sensitive fluid, for example the temperature sensitive fluid may change color upon reaching a specified temperature. The color change may either be sensed by device or provide the user an indication to pause the treatment. The temperature sensitive fluid may be applied by the user or dispensed from fluid dispenser 180.

Fluid dispenser 180 may comprise an actuator arranged to release specified amounts of the fluid, either by the user or automatically by device 100 in relation to various treatment parameters (e.g., treated area, movement intensity, delivered energy, elapsed time, measured temperature). Control unit 150 may release fluid with respect to measurements by either sensors 120, 140.

In certain embodiments, the gel may be a dermabrasion gel which may serve both as a contact enhancer, to assure proper energy delivery (e.g., RF) to the tissue, as well as an active dermabrasion compound for epidermal skin rejuvenation. The dermabrasion effect may be enhanced by the heating by device 100, e.g., heating sand-like particles in the gel may enhance their abrasion and cleansing properties.

In certain embodiments, the gel may be provided in a tube, and can be designed to last for a specified number of treatments (e.g., approximately 20 full treatments).

In certain embodiments, skin treatment with device 100 may be combined with any other treatment method, e.g., light or ultrasound delivery, application of gels, creams, topical formulations etc.

In certain embodiments, skin treatment with device 100 may comprise a vibration module 170 arranged to vibrate device 110 to influence treatment efficiency. For example, vibration may be arranged to assist spreading and evening heat application to the treated skin, spread a fluid applied to the skin, improve temperature or motion measurements or indicate certain temperature or motion threshold to the user. For example, while device 100 may stop heating beyond certain thresholds, device 100 may indicate approaching these thresholds by vibration. For example, the user may be instructed to apply a treatment gel to the electrodes, then to push a trigger button/switch, and then treat the skin in a circulatory movement (for example) for 4 minutes per treatment area (for example). At the end of 4 minutes (exemplary time period), the user feels a mild vibration and RF emission stops. The procedure can then be repeated for any and all treatment areas.

Figure 6:
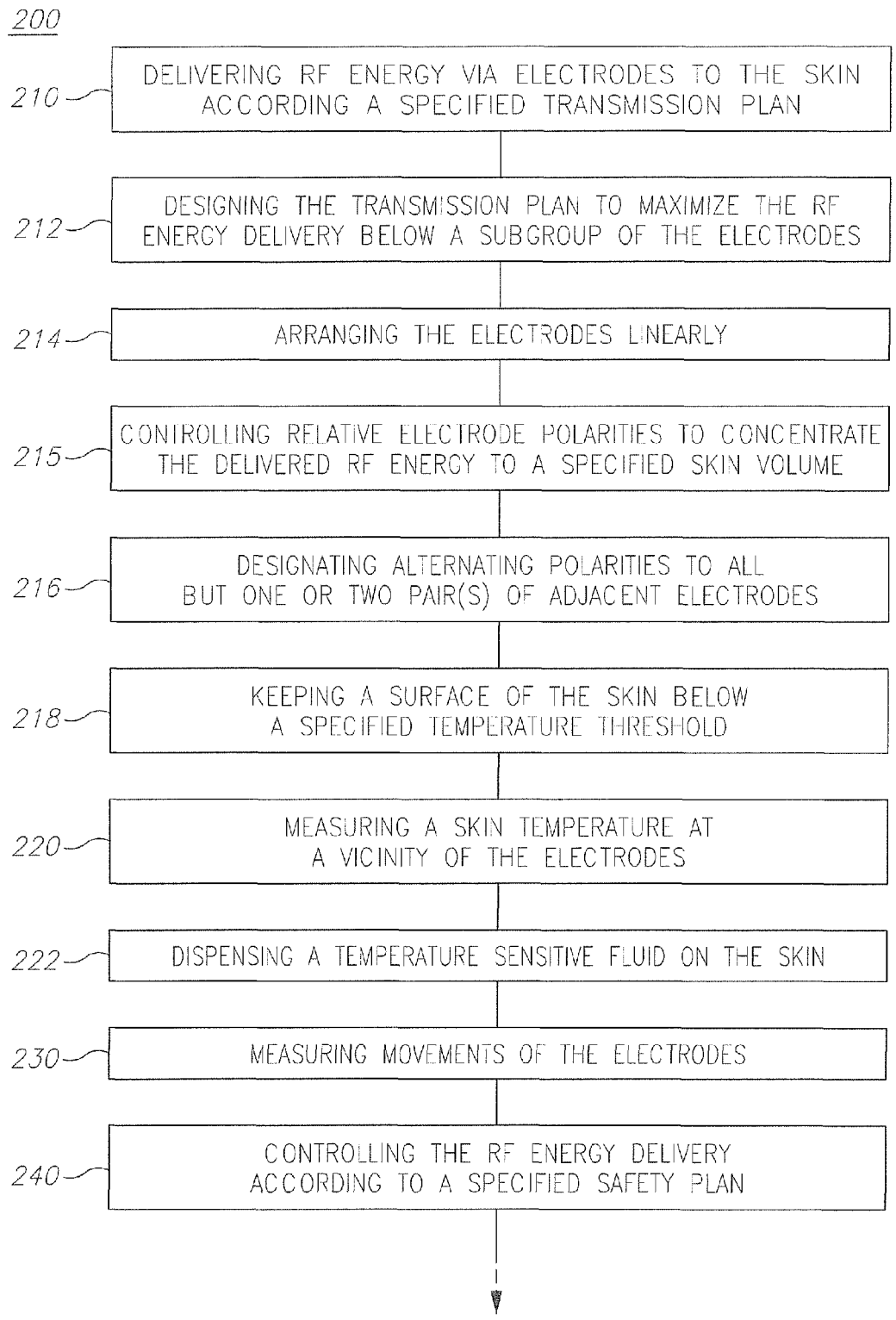
FIG. 6 is a high level schematic flowchart illustrating a skin treatment method according to some embodiments of the invention.

FIG. 6 is a high level schematic flowchart illustrating a skin treatment method 200 according to some embodiments of the invention.

Method 200 may comprise delivering RF energy via electrodes to the skin according a specified transmission plan (stage 210) and controlling the RF energy delivery according to a specified safety plan (stage 240).

In certain embodiments, method 200 comprises designing the transmission plan to maximize the RF energy delivery below a subgroup of the electrodes (stage 212) and controlling relative electrode polarities to concentrate the delivered RF energy to a specified skin volume (stage 215), for example arranging the electrodes linearly (stage 214), and designating alternating polarities to all but one or two pairs of electrodes (stage 216). The transmission plan may be designed to concentrate the delivered RF energy to a specified skin volume below the one or two pairs of adjacent electrodes having the same polarity. Method 200 further comprises keeping a surface of the skin below a specified temperature threshold (stage 218).

In certain embodiments, method 200 comprises measuring a skin temperature a vicinity of the electrodes (stage 220), measuring movements of the electrodes (stage 230) and designing the safety plan to prevent overheating of a specified skin surface area (stage 242) and for RF energy delivery by an unskilled user (stage 244). The safety plan may comprise stopping RF energy delivery upon a temperature measurement higher than a specified threshold (stage 246) and/or stopping RF energy delivery upon a lack of movement for a time period longer than a specified duration (stage 248).

In certain embodiments, method 200 further comprises indicating a measured temperature approaching the specified threshold (stage 256) and/or indicating a time period of missing motion approaching the specified duration (stage 258).

In certain embodiments, method 200 further comprises dispensing a temperature sensitive fluid on the skin (stage 222). Temperature sensitive fluid may indicate the skin surface temperature to prevent surface overheating. Method 200 may further comprise using or dispensing any fluid, gel, cream or topical formulation to enhance skin treatment.

Exemplary Clinical Data is presented in the following. The safety and efficacy of embodiments of the skin treatment device according to some embodiments of the present disclosure were evaluated in clinical study, based on the PRE IDE protocol approved by the FDA. Six (6) treatments and one follow-up visit were conducted per each subject with six (6) body area categories being treated: abdomen, thighs, arm, buttock, saddle bags and décolleté. In order to evaluate treatment efficacy, pre and post treatment photos were introduced to two uninvolved physicians for blinded evaluation. A total of 30 subjects were recruited to the study. No adverse side effects were detected or reported. All 30 patients participating in the study reported no pain during the treatment. Photographic analysis of pre- and post-treatment of the digital images were conducted by two blinded board certified dermatologists. Analysis revealed improvement (downgrade of at list 1 score according to the Fitzpatrick scale) in vast majority patients (83.6% improvement at last follow-up visit according to first reviewer and 96.7% improvement according to the second reviewer). Score differences were found to be statistically significant while comparing baseline score to the scores obtained following 6 treatments (p<0.001), and last follow-up visit (p<0.001) for both reviewers, indicating treatment efficacy.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A skin treatment device comprising:
a plurality of linearly arranged electrodes adapted to directly contact a contacting surface of a user's skin non-invasively;
a radio frequency (RF) generator, arranged to deliver RF energy to the skin via the electrodes; and
a control unit arranged to control RF energy delivery by the RF generator to the skin according to a specified transmission plan, the specified transmission plan comprising controlling relative electrode polarities to yield at least one pair of adjacent electrodes with the same polarity to concentrate the delivered RF energy to a specified skin volume at a predetermined depth below the electrodes, wherein the control unit is adapted to elevate a temperature of the specified skin volume with respect to the contacting surface of the skin, while keeping the contacting surface of the skin below a specified temperature threshold.

2. The skin treatment device of claim 1, further comprising a fluid dispenser arranged to dispense, upon actuation, a fluid on the skin.

3. The skin treatment device of claim 1, further comprising:
a temperature sensor positioned in a vicinity of the electrodes; and
a motion sensor arranged to measure movements of the electrodes with respect to the skin,
wherein the control unit is further arranged to control RF energy delivery with respect to measurements obtained from the temperature and motion sensors according to a specified safety plan designed to prevent overheating of a specified skin surface area upon operation of the device by an unskilled user.

4. The skin treatment device of claim 3, wherein the control unit is further arranged to stop energy delivery upon detection of a non-changing measurement from at least one of the temperature sensor and the motion sensor.

5. The skin treatment device of claim 3, wherein the temperature sensor separates the electrodes into two groups, one of which comprising an adjacent pair of electrodes with the same polarity.

6. The skin treatment device of claim 3, wherein the specified safety plan comprises stopping RF energy delivery upon detection of a temperature measurement higher than a specified threshold or a lack of movement for a time period longer than a specified duration.

7. The skin treatment device of claim 6, further comprising an indicator arranged to indicate the detection.

8. The skin treatment device of claim 3, wherein the temperature sensor comprises a temperature sensitive fluid applied on the skin from the fluid dispenser.

9. The skin treatment device of claim 3, further comprising at least one additional temperature sensor.

10. The skin treatment device of claim 3, wherein the motion sensor is an accelerometer positioned within the device.

11. A skin treatment method comprising delivering RF energy via a plurality of linearly arranged electrodes to a contacting surface of a user's skin, non-invasively, wherein the electrodes contact the contacting surface of the skin, according to a specified transmission plan, the specified transmission plan comprising controlling relative electrode polarities to yield at least one pair of adjacent electrodes with the same polarity to concentrate the delivered RF energy to a specified skin volume at a predetermined depth below the electrodes, to elevate thereby elevating a temperature of the specified skin volume with respect to the surface of the skin while keeping the contacting surface of the skin, which contacts the electrodes, below a specified temperature threshold.

12. The skin treatment method of claim 11, further comprising:
measuring a skin temperature a vicinity of the electrodes;
measuring movements of the electrodes; and
controlling the RF energy delivery with respect to the measurements according to a specified safety plan designed to prevent overheating of a specified skin surface area upon carrying out the RF energy delivery by an unskilled user.

13. The skin treatment method of claim 12, wherein the specified safety plan is further designed to stop energy delivery upon detection of a non-changing temperature or movement measurement.

14. The skin treatment method of claim 12, wherein the specified safety plan is further designed to stop RF energy delivery upon at least one of: a temperature measurement higher than a specified threshold and a lack of movement for a time period longer than a specified duration.

15. The skin treatment method of claim 14, further comprising indicating at least one of: a measured temperature approaching the specified threshold and a time period of missing motion approaching the specified duration.

16. A skin treatment device comprising:
- a plurality of linearly arranged electrodes adapter to directly contact a contacting surface of a user's skin, non-invasively;
- a radio frequency (RF) generator, arranged to deliver RF energy to the skin via the electrodes;
- a temperature sensor positioned in a vicinity of the electrodes;
- a motion sensor arranged to measure movements of the electrodes with respect to the skin; and
- a control unit arranged to:
  control RF energy delivery by the RF generator to the skin according to a specified transmission plan comprising controlling relative electrode polarities to yield at least one pair of adjacent electrodes with substantially the same polarity to concentrate the delivered RF energy to a specified skin volume at a predetermined depth below the electrodes to elevate a temperature of the specified skin volume with respect to the surface of the skin and keep a contacting surface of the skin, which contacts the electrodes, below a specified temperature threshold; and
  control RF energy delivery with respect to measurements obtained from the temperature and motion sensors according to a specified safety plan designed to prevent overheating of a specified skin surface area upon operation of the device by an unskilled user, to stop energy delivery upon detection of at least one of:
  - a temperature measurement higher than a specified threshold;
  - a lack of movement for a time period longer than a specified duration; and
  - a non-changing measurement from at least one of the temperature sensor and the motion sensor.

* * * * *